United States Patent [19]

Patnaik et al.

[11] Patent Number: 5,855,618
[45] Date of Patent: Jan. 5, 1999

[54] POLYURETHANES GRAFTED WITH POLYETHYLENE OXIDE CHAINS CONTAINING COVALENTLY BONDED HEPARIN

[75] Inventors: Birendra K. Patnaik, Chester; Richard J. Zdrahala, Montville, both of N.J.

[73] Assignee: Meadox Medicals, Inc., Oakland, N.J.

[21] Appl. No.: 713,803

[22] Filed: Sep. 13, 1996

[51] Int. Cl.$^6$ ...................................................... A61F 2/02
[52] U.S. Cl. ................. 623/11; 623/1; 427/2.24; 427/2.25
[58] Field of Search ................ 623/1, 11; 427/2.24, 427/2.25

[56] References Cited

U.S. PATENT DOCUMENTS

| | | |
|---|---|---|
| 4,229,838 | 10/1980 | Mano . |
| 4,331,697 | 5/1982 | Kudo et al. . |
| 4,600,652 | 7/1986 | Solomon et al. ......................... 623/11 |
| 4,613,517 | 9/1986 | Williams et al. . |
| 4,642,242 | 2/1987 | Solomon et al. . |
| 4,678,660 | 7/1987 | McGary et al. . |
| 4,713,402 | 12/1987 | Solomon . |
| 4,720,512 | 1/1988 | Hu et al. . |
| 4,786,556 | 11/1988 | Hu et al. . |
| 4,973,493 | 11/1990 | Guire . |
| 4,979,959 | 12/1990 | Guire . |
| 5,061,777 | 10/1991 | Yoda et al. . |
| 5,077,352 | 12/1991 | Elton . |
| 5,077,372 | 12/1991 | Hu et al. . |
| 5,132,108 | 7/1992 | Narayanan et al. . |
| 5,134,192 | 7/1992 | Feijen et al. . |
| 5,171,264 | 12/1992 | Merrill ........................................ 623/1 |
| 5,258,041 | 11/1993 | Guire et al. . |
| 5,409,696 | 4/1995 | Narayanan et al. . |
| 5,451,424 | 9/1995 | Solomon et al. . |
| 5,728,751 | 3/1998 | Patnaik ........................................ 623/1 |

OTHER PUBLICATIONS

Heparin Immobilization onto Segmented Polyurethaneurea Surfaces–Effect of Hydrophilic Spacers, by Ki Dong Park, Teruo Okano, Chisato Nojiri, and Sung Wan Kim, Journal of Biomedical Materials Research, vol. 22, pp. 977–992 (1988).

SPUU–PEO–Heparin Graft Copolymer Surfaces, Patency and Platelet Deposition in Canine Small Diameter Arterial Grafts by Won Gon Kim Ki Dong Park, Syed F. Mohammad, and Sung Wan Kim, ASA10 Trans., (1991), 37: M148–149.

Synthesis and Characterization of SPUU–PEO–Heparin Graft Copolymers, by Ki Dong Park, Al Zhi Piao, Harvey Jacobs, Teruo Okano and Sung Wan Dim, Journal of Polymer Science: Part A: Polymer Chemistry; vol. 29, pp.1725–1737 (1991).

PEO–Modified Surfaces–In Vitro. Ex Vivo, and In Vivo Blood Compatibility by Ki Dong Park and Sung Wan Kim Poly (Ethylene Glycol) Chemistry: Biotechnical and Biomedical Applications, pp. 283–301 (1992).

In Vivo Nonthrombogenicity of Heparin Immobilized Polymer Surfaces by Chisato Nojiri, Ki Dong Park, David W. Grainger, Harvey A. Jacobs, Teruo Okano, Hitoshi Koyanagi, and Sung Wan Kim, pp. M168–M172, ASA10 Trans. (1990), vol. 36.

*Primary Examiner*—Paul B. Prebilic
*Attorney, Agent, or Firm*—Hoffmann & Baron, LLP

[57] ABSTRACT

Disclosed are bio-active polymer coatings. More particularly, improved bio-active polymer coating are disclosed which include bio-active molecules attached to polyurethane backbones via amine-terminated spacers. Also disclosed are novel reaction schemes for producing same.

8 Claims, No Drawings

POLYURETHANES GRAFTED WITH POLYETHYLENE OXIDE CHAINS CONTAINING COVALENTLY BONDED HEPARIN

FIELD OF INVENTION

The present invention relates generally to bio-active polymer coatings. More particularly, the present invention relates to an improved bio-active polymer coating including a bio-active molecule attached to a polyurethane backbone via an amine-terminated spacer.

BACKGROUND OF THE INVENTION

It is well known to use bio-active materials to coat structures to be introduced into a living system. Over the last 30 years, research into this area has become increasingly important with the development of various bio-compatible articles for use in contact with blood, such as, for example, vascular grafts, artificial organs, endoscopes, cannulas, and the like.

While various materials have been used to make such articles, synthetic polymers have been increasingly popular as the preferred materials due to their anti-thrombogenic and good mechanical properties. For example, polyurethane is a useful and effective material with a variety of clinical applications. Although synthetic polymers, such as, PTFE and polyurethane, are less thrombogenic than earlier materials, thrombus formation is still a problem. A thrombus is the formation of a solid body composed of elements of the blood, e.g., platelets, fibrin, red blood cells, and leukocytes. Thrombus formation is caused by blood coagulation and platelet adhesion to, and platelet activation on, foreign substances. Thus, thrombus formation is a serious complication in surgery and clinical application of artificial organs.

Various anti-thrombogenic agents, such as, heparin, have been developed and incorporated into bio-compatible articles to combat thrombus formation. In a living system, heparin inhibits the conversion of a pro-enzyme (prothrombin) to its active form (thrombin). Thrombin catalyzes a complicated biochemical cascade which ultimately leads to the formation of a thrombus.

Infection is also a serious concern for articles to be implanted into a host organism. Bacterial, viral and other forms of infection may lead to life-threatening complications when an article is implanted into a host organism. Thus, binding of an anti-infection agent to a surface of an implantable article can reduce the risk of infection when an article is introduced into a host organism.

The art is replete with various procedures for grafting bio-active molecules onto polymer surfaces to prevent thrombus formation and/or infection. For example, biocompatible polymer surfaces have been described with various benefits including decreased thrombogenicity, increased abrasion-resistance and improved hydrophilic lubricious properties. Alternatively, preparing polymeric surfaces to receive bio-active agents by plasma treatment is also well known in the art.

Various polyurethane coatings to which bio-active agents are added have also been described. For example, bio-active agents directly bound to the polymer backbone of a polymer coating material are known. Also, polymer coatings are described that include either covalently or jonically binding bio-active agents to substrate surfaces. For example, photochemical reactions are described which covalently bind bio-active agents to substrate surfaces. Also, quarternary ammonium reagents are described which ionically bind a bio-active agent to a substrate. In polyurethane coatings, various spacer molecules that link bio-active agents to polymer substrates have been described by several studies. These studies indicate that bio-active agents, such as, for example, heparin bound to polymer coatings, retain more of their activity if they are tethered away from the surface of an article by a spacer.

Various substrate surfaces have previously been described that are suitable for introducing into a biological system. For example, Yoda et al. in U.S. Pat. No. 5,061,777 disclose that polyurethanes and polyurethaneureas containing both hydrophilic and hydrophobic polyether segments are more anti-thrombogenic than substrates produced from either a hydrophilic or a hydrophobic polyol exclusively. Similarly, Elton in U.S. Pat. No. 5,077,352 discloses a method of forming a mixture of an isocyanate, a polyol and a poly (ethylene oxide) in a carrier liquid. This mixture is then heated and cured to form a coating of a polyurethane complexed with a poly(ethylene oxide) having good adherence to a substrate and good anti-friction properties.

A significant limitation of these bio-compatible polymer surfaces, however, is that they are not completely biocompatible. Thrombus formation and infection continue to pose problems when an article is implanted within a host using these bio-compatible polymer surfaces. Thus, various alternative methods have been described for preparing the surface of an article to be implanted in a host organism to accept bio-active agents. Plasma treatment of substrate surfaces is one such method.

For example, Hu et al. in U.S. Pat. No. 4,720,512 disclose a method for imparting improved anti-thrombogenic activity to a polymeric support structure by coating it with an amine-rich material, e.g., a polyurethaneurea, introducing hydrophobic groups into the amine-rich surface coating through plasma treatment with fluorine compounds, and covalently bonding an anti-thrombogenic agent to the hydrophobic amine-rich surface. Similarly, Hu et al. in U.S. Pat. No. 4,786,556 disclose substituting siloxane and silazane compounds during the plasma treatment step of the '512 patent for the previously disclosed fluorine compounds. See also, Narayanan et al. in U.S. Pat. No. 5,132,108 and 5,409,696 and Feijen et al. in U.S. Pat. No. 5,134,192 for other examples of plasma treating substrates prior to introduction of a bio-active molecule.

These preceding methods for plasma treating a substrate surface are limited in their scope because they only work with certain substrates. Thus, they do not provide a general purpose coating composition that can bind to a variety of substrate surfaces. In an alternate approach, however, various methods have been described for binding bio-active agents directly to substrate surfaces.

For example, Solomon et al. in U.S. Pat. No. 4,642,242 disclose a process for imparting anti-thrombogenic activity to a polyurethane polymer material by coating a support structure with a protonated amine-rich polyurethaneurea, activating the amine moiety with an alkaline buffer, and covalently linking an anti-thrombogenic agent, e.g., heparin, to the polyurethaneurea with a reducing agent.

Hu et al. in U.S. Pat. No. 5,077,372 disclose a medical device having a hemocompatible polyurethaneurea surface coating that is produced by reacting a diisocyanate, a polyamine and a mixture of fluorinated and nonfluorinated polyols, and an anti-thrombogenic agent covalently linked to the amino groups of the polyurethane coating. These coating reactions and heparinizations are carried out directly on the device's surface.

Bio-active agents bound directly to polymer backbones suffer from several limitations. First, because these bio-active agents are directly linked to the polymer backbone, their in vivo mobility is decreased. Second, the process of linking the bio-active agent to the polymer backbone may diminish the number of functional binding sites on the bio-active agent. Third, the bio-active agent's close proximity to the polymer backbone limits its ability to interact with its physiological substrates. Thus, for all of these reasons, coatings containing bio-active molecules bound directly to the polymer backbone are limited by the bio-active agent's decreased activity.

Accordingly, alternative methods have been developed for binding bio-active molecules to substrate surfaces. In particular, methods for ionically binding bio-active agents to a substrate via a quaternary ammonium compound have been described. See for example, Mano in U.S. Pat. No. 4,229,838, Williams et al. in U.S. Pat. No. 4,613,517, McGary et al. in U.S. Pat. No. 4,678,660, Solomon et al. in U.S. Pat. No. 4,713,402, and Solomon et al. in U.S. Pat. No. 5,451,424.

These methods, however, are severely limited because the bio-active agent is leached over time from the surface of the substrate. Thus, the protection afforded by the ionically bound bio-active agent to the substrate surface is transient at best. Accordingly, more permanent methods for binding bio-active molecules to substrate surfaces have also been developed. These methods include covalently binding a bio-active molecule, either directly, or via a spacer molecule, to a substrate surface.

For example, photochemical reactions have been described for preparing substrate surfaces to receive anti-thrombogenic agents. Kudo et al. in U.S. Pat. No. 4,331,697 disclose a method for imparting anti-thrombogenic activity to a biomedical material by directly linking a heparin derivative to the surface of the material via actinic radiation. Similarly, Kudo et al. also disclose coating a surface of a biomedical material with a polymer having a carboxylic acid halide group and/or a carboxylic anhydride functional group as a side chain that can react with a heparin derivative.

Alternatively, Guire et al. in U.S. Pat. Nos. 4,973,493 and 4,979,959 disclose methods for binding bio-active molecules to substrates using a linking moiety with functionalized end groups preferably that are activated by different signals. The linking moiety can covalently bind a bio-active molecule upon introduction of a first activation signal which activates the first functionalized end group. The linking moiety is further capable of covalently binding to the substrate upon introduction of a second, different, signal (photochemical) which activates the second functionalized end group. Similarly, Guire et al. in U.S. Pat. No. 5,258,041 further define the spacer molecule of their '493 and '959 patents.

Lastly, Bichon et al. in U.S. Pat. No. 4,987,181 disclose a substrate having an adhesive film with anti-thrombogenic properties on its surface. This adhesive film is an olefinic copolymer having carboxylic side chains of the formula $O=CH-NH_2-(CH_2)_n-NH_2-CH_2-R$, wherein R is a heparin molecule or a depolymerization fragment of a heparin molecule. The adhesive film is deposited onto the substrate via photo-initiated polymerization of a suitable monomer. Thus, heparin, or a fragment thereof, is covalently linked to the substrate via an amine spacer.

Although spacer molecules provide a means for optimizing the bio-activity of bio-agents bound to substrate surfaces, several problems persist in the photochemical reactions used to bind these bio-active molecules via spacers to substrate surfaces. Included among these problems are the ability of the bio-active molecule to withstand the photochemical signal used to bind it to the substrate surface, as well as the ability of the substrate to withstand photoradiation. For example, inert polymeric substrates, e.g., polytetrafluoroethylene, degrade when exposed to photochemical reactions and cannot be used therewith. Thus, attempts have been made to use spacer molecules to bind bio-active agents to substrate surfaces without photochemical reactive groups.

For example, in a four step process, Park et al. disclose immobilizing heparin onto a commercial preparation of a segmented polyetherurethaneurea (PUU) using hydrophilic poly(ethylene oxide) (PEO) spacers of different molecular weights. Their method includes (1) coupling hexamethyldiisocyanate (HMDI) to a segmented polyurethaneurea backbone through an allophanatelbiuret reaction between the urethane/urea-nitrogen proton and one of the isocyanate groups on the HMDI. Next, (2) the free isocyanate groups attached to the backbone are then coupled to a terminal hydroxyl group on a PEO to form a PUU-PEO complex. Next (3) the free hydroxyl groups of the PUU-PEO complex are treated with HMDI to introduce a terminal isocyanate group. Finally, (4) the NCO functionalized PUU-PEO is then covalently bonded to reactive functional groups on heparin ($-OH$ and $-NH_2$) producing a PUU-PEO-Hep product. K. D. Park and S. W. Kim, "PEO-Modified Surfaces-In Vitro, Ex Vivo and In Vivo Blood Compatibility", in Poly(Ethylene Glycol) Chemistry: Biotechnical and Biomedical Applications 283 (J. Milton Harris ed. 1992). This method will be referred to hereinafter as the "Park Method."

All of these disclosures have addressed substrate surfaces and/or coatings therefor which can exist within biological systems and in particular, can increase the anti-thrombogenicity of the surface of, e.g., medical articles. These reactions are generally slow, multi-step syntheses, and are characterized by side reactions which lead to low yields and formation of cross-linked polymers. In addition, these reactions cannot be universally applied to substrate surfaces. Thus, in particular, there is a need for a bio-active coating and process that can be used with a broad spectrum of substrate surfaces. In addition, there is a need particularly for a coating process that uses a hydrophilic amine-terminated spacer to maximize the bio-activity of the bio-active agent. There is also a need for a simplified bio-active coating process that provides a higher yield of polymer with negligible cross-linking in a shorter period of time. The present invention is directed toward providing a solution therefor.

SUMMARY OF THE INVENTION

The present invention relates to a bio-active coating that includes a first reaction in which a bio-compatible backbone is reactive with a hydrophilic, amine-terminated spacer in the presence of a first dehydrating agent. The bio-compatible backbone contains one or more functional groups chosen from any number of useful carboxyl functionalities, unsaturated functionalities and mixtures thereof. In addition, the spacer has first and second ends in which each end has at least one amine group attached thereto. Furthermore, one of the amine groups of the spacer is reactive with one or more of the functional groups on the backbone in the presence of a dehydrating agent. Also, a second reaction is provided that includes reacting a bio-active agent with the remaining unreacted amine-terminated end of the spacer in the presence of a second dehydrating agent. This second reaction covalently binds the bio-active agent to the polymer backbone.

The polymer backbone may be chosen from any number of useful polyurethane materials provided the requisite functionality is present. The polyurethane backbone is preferably a polyesterurethaneurea. For example, one useful polyurethane is a commercially available segmented polyurethaneurea known as BIOSPAN® available from the Polymer Technology Group, Inc., Emeryville, Calif.

The hydrophilic amine-terminated spacer may include oxygenated polyolefins, aliphatic polyesters, polyamino acids, polyamines, hydrophilic polysiloxanes, hydrophilic polysilazanes, hydrophilic acrylates, hydrophilic methacrylates, linear and lightly branched polysaccharides. Preferably, the hydrophilic amine-terminated spacer is an amino end blocked poly(ethylene oxide) (PEO).

It is thought that hydrophilic PEO spacers increase the bio-activity of, e.g., heparin, due to the PEO's low interfacial free energy, its lack of binding sites and its highly dynamic motions. The hydrophilic spacer is bound to a bio-active agent. This spacer/bio-active agent (SBA) complex is repelled by the usually hydrophobic substrate surface. Thus, the repulsive force generated between the hydrophilic SBA complex and the hydrophobic substrate surface positions the bio-active agent at a distance from the substrate surface. This positioning is important because studies have shown that the bio-activity of heparin bound to a spacer increases as the chain length of the spacer increases. For example, in an in vitro comparison of the bio-activity of heparin attached to a $C_6$ alkyl spacer and PEO spacers of varying lengths (PEO 200, PEO 1,000 and PEO 4,000), the longest PEO spacer-heparin molecule (PEO 4000) demonstrated the highest heparin bio-activity. See, K. D. Park et al., supra.

Thus, one way the degree of activity of the active agent may be controlled is by varying the distance between it and the polyurethane backbone via hydrophilic spacer molecules, e.g., PEO. Such control is achieved by varying the length of the hydrophilic amine-terminated spacer.

Thus, the hydrophilic amine-terminated spacer of the present invention may have a molecular weight of about 100 daltons to about 200,000 daltons. Preferably, the hydrophilic amine-terminated spacer has a molecular weight of about 200 to about 50,000 daltons. More preferably, the hydrophilic amine-terminated spacer has a molecular weight of about 1,000 daltons to about 10,000 daltons. Most preferably the hydrophilic amine-terminated spacer has a molecular weight of about 4,000 daltons.

It is further contemplated to position the bio-active agent at a bio-effective distance from the polymer backbone by varying the molecular weight of the hydrophilic amine-terminated spacer. In this way, the activity of the bio-active agent may be controlled simply by choosing the appropriate spacer.

As used herein, the term "bio-active agent" is intended to mean any agent that is reactive with a primary amine to form a stable bond, is active upon introduction into a living system and enhances the bio-compatibility of any article introduced therein. Thus, the term "bio-active agent" includes anti-thrombogenic agents, such as, heparin, prostaglandins, urokinase, streptokinase, sulfated polysaccharide, albumin, etc., their pharmaceutical salts and mixtures thereof. In the present invention, "bio-active agent" also includes anti-infective agents including, for example, antibiotics, antibacterial agents, antiviral agents, antimicrobial agents, their pharmaceutical salts and mixtures thereof. The present invention also contemplates using mixtures of anti-thrombogenic agents and anti-infective agents. Heparin and its pharmaceutical salts, however, are the preferred embodiment of the invention.

In the present invention, both the first and second reactions are facilitated by a dehydrating agent. The dehydrating agent may be any useful dehydrating agent that can facilitate these reactions such as, for example, dicyclohexyl carbodiimide. Only 1-(3-dimethylaminopropyl)-3-ethylcarbodiimide hydrochloride (EDC), however, has the proper reactivity and solubility to permit its use in an aqueous system, such as, the heparin coupling reaction of the present invention.

In another embodiment of the invention, a coating composition is provided that includes a polymeric structure defined by a bio-compatible backbone having at least one pendant moiety selected from the group consisting of $R^1$—$R^2$—NH—C—$R^3$, wherein $R^1$ is O=C—NH or NH; $R^2$ is a hydrophilic spacer moiety selected from the group consisting of oxygenated polyolefins, aliphatic polyesters, polyamino acids, polyamines, hydrophilic polysiloxanes, hydrophilic polysilazanes, hydrophilic acrylates, hydrophilic methacrylates, linear and lightly branched polysaccharides; and $R^3$ is a bio-active agent selected from the group consisting of antithrombogenic agents, antibiotic agents, antibacterial agents, antiviral agents, their pharmaceutical salts and mixtures thereof. Heparin and its pharmaceutical salts, however, are the preferred embodiment of bio-active agent of the invention.

In a preferred embodiment, the polymeric structure takes the form of a "comb" configuration, whereby multiple pendant moieties as described above emanate from the backbone like teeth on a comb. These moieties carry at their free terminal end the bio-active agent, which is tethered away from the polymer backbone to make the bio-active agent more accessible to blood, and concurrently to protect against the formation of thrombi.

In a further aspect of this embodiment, the spacer moiety $R^2$ may be an amino end-blocked poly(ethylene oxide). The amino end-blocked poly(ethylene oxide) may have a molecular weight of about 100 daltons to about 200,000 daltons. Preferably, the amino end-blocked poly(ethylene oxide) has a molecular weight of about 200 to about 50,000 daltons. More preferably, the amino end-blocked poly(ethylene oxide) has a molecular weight of about 1,000 daltons to about 10,000 daltons. Most preferably the amino end-blocked poly(ethylene oxide) has a molecular weight of about 4,000 daltons.

It is further contemplated to position the bio-active agent at a bio-effective distance from the polymer backbone by varying the molecular weight of the hydrophilic amine-terminated spacer. In this way, the activity of the bio-active agent may be controlled simply by choosing the appropriate spacer.

Preferably, the polymeric backbone is a polytetramethyleneoxide-based aromatic polyurethaneurea with mixed aliphatic and cycloaliphatic diamine chain extenders. Most preferably, the polymeric backbone is a polyesterurethaneurea. For example, one useful commercially available polymeric backbone is BIOSPAN®. In one embodiment of the present invention, a polymer backbone is synthesized which contains $CO_2H$ functionality. In another embodiment, a polymer backbone is synthesized which contains an unsaturated functionality, such as, for example $HO_2CH=CH—CO_2H$.

In yet another embodiment of the invention, a method for preparing a bio-active coating is provided wherein a bio-active group is covalently bonded through a spacer to a polymer backbone. This method includes providing a unsaturated carboxyl functionality or a saturated functionality-containing polyurethane prepolymer backbone, reacting the backbone with a hydrophilic amine-terminated spacer in the presence of a first dehydrating agent whereby the spacer is covalently attached on the backbone as a pendant group, and further reacting the pendant group with a bio-active agent in the presence of a second dehydrating agent whereby the bio-active agent is covalently bound to the pendant group.

Both the first and second reactions are facilitated by a dehydrating agent. Preferably, the dehydrating agent is EDC in both reactions. Other dehydrating agents, as previously described, may also be employed to facilitate such reactions. Only EDC, however, has the proper reactivity and solubility to permit its use in an aqueous system as described by the present invention.

In a further embodiment of the invention, a polymer-bound bio-active composition is represented by the following structure:

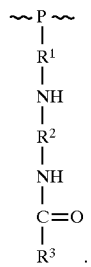

wherein P is a bio-compatible polymer selected from the group consisting of bio-compatible polymers having unsaturated carboxyl functionality, saturated functionality and mixtures thereof; $R^1$ is O=C—NH or NH; $R^2$ is a hydrophilic amine-terminated spacer selected from the group consisting of oxygenated polyolefins (e.g., polyvinyl alcohol), aliphatic polyesters, polyamino acids, polyamines, hydrophilic polysiloxanes, hydrophilic polysilazanes, hydrophilic acrylates, hydrophilic methacrylates, and linear or lightly branched polysaccharides; and $R^3$ is a bio-active agent selected from the group consisting of anti-thrombogenic agents, antibiotic agents, antibacterial agents, antiviral agents, their pharmaceutical salts, and mixtures thereof. Preferably, however, $R^3$ is heparin or one of its pharmaceutical salts.

In this bio-active coating, P may be chosen from any number of useful polyurethane materials provided the requisite functionality is present. P is preferably a polyesterurethaneurea. Most preferably, P is a commercially available polyurethaneurea known as BIOSPAN®.

Preferably, the spacer $R^2$ is an amino end-blocked poly(ethylene oxide). This amino end-blocked poly(ethylene oxide) may have a molecular weight of about 100 daltons to about 200,000 daltons, with preferred molecular weights as described herein.

The bio-active agent ($R^3$) may be positioned at an effective distance from P by varying the molecular weight, and as a consequence, the chain length of $R^3$. In this way, the activity of $R^3$ may be enhanced and controlled by choosing the appropriate spacer.

In yet another embodiment of the invention, a method is included for contacting an article with the bio-active coating. Preferably, the article is dipped or steeped in an aqueous solution of the polymer bound bio-active coating. The article of the present invention may be any medical device. Preferably, the article is an implantable medical device, such as, for example, a vascular graft, catheter, stent, endoprosthesis and the like.

Thus, the invention provides a bio-active coating, a coating composition and methods for preparing same.

DETAILED DESCRIPTION OF THE INVENTION

While this invention is satisfied by embodiments in many different forms, there will be described herein in detail preferred embodiments of the invention, with the understanding that the present disclosure is to be considered as exemplary of the principles of the invention and is not intended to limit the invention to the embodiments illustrated and described. The scope of the invention will be measured by the appended claims and their equivalents.

In accordance with the present invention, novel bio-active coatings and their use in developing anti-thrombogenic and/or anti-infective articles are provided. More particularly, new reaction schemes are provided for the synthesis of heparinized polyurethanes. Also provided are methods for using the heparinized polymers as antithrombogenic coatings on, e.g., small caliber ePTFE vascular grafts.

The bio-active coatings and methods described herein are particularly advantageous over previously disclosed polymer coatings because the composition and structure of the present coatings are more controllable and reproducible. In addition, the properties of the bio-active coatings of the present invention can be varied easily, e.g., biostability, hydrophilicity etc. Also, the methods of synthesizing the present bio-active coatings are more efficient and take less time than previously disclosed methods. Another advantage of the present invention is that the reactions may be carried out at lower temperatures. Importantly, the reaction schemes of the present invention form fewer cross-links and provide higher polymer yields than previously described methods.

The polymer backbones of the present invention are comb-type polymers in which bio-active molecules, such as heparin, are attached. Preferred polymers are siloxane-urethane copolymers, or most preferably, polyurethanes and polyurethaneureas.

A composition of the invention was synthesized by reacting a polyol and a methyl diisocyanate to form a prepolymer. This prepolymer was reacted with a chain extender in the presence of a saturated carboxylic acid. Preferably, the saturated carboxylic acid is

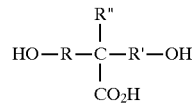

where R is an alkyl of 1–10 carbon atoms; R' is an alkyl of 1–10 carbon atoms; and R" is an alkyl or aryl of 1–10 carbon atoms. Preferably, R=R'=CH and R"=CH$_3$. More preferably, the chain extender is butanediol (BDO). The resulting product was a polyurethane polymer containing carboxyl functionality (I). This polymer was then added to a hydrophilic amine-terminated poly(ethylene oxide) (II) in the presence of a dehydrating agent as indicated below:

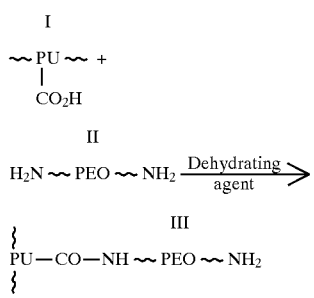

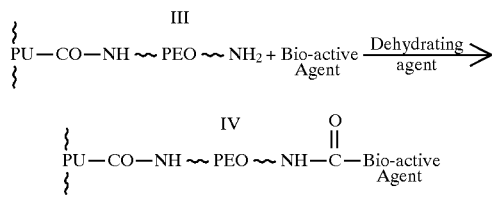

The product (III) of the reaction indicated above is a polymer-spacer complex characterized by an amide linkage between the spacer and the polymer and an amine group on the free terminal end of the spacer. A bio-active agent, such as heparin, is then covalently bound to the polymer-spacer complex in the presence of a dehydrating agent, such as, EDC, as indicated below:

$$\overset{\}{\underset{\}{PU}}-CO-NH\sim PEO\sim NH_2 + \text{Bio-active Agent} \xrightarrow[\text{agent}]{\text{Dehydrating}}$$

$$\overset{\}{\underset{\}{PU}}-CO-NH\sim PEO\sim NH-\overset{O}{\overset{\|}{C}}-\text{Bio-active Agent}$$

The product (IV) of the reaction indicated above is characterized by an amide linkage between the spacer and the bio-active molecule, e.g., heparin. Thus, in this embodiment, the reaction product (IV) is characterized by amide linkages between its respective units, i.e., between the polyesterurethane backbone and the spacer, and between the spacer and the bio-active agent. This composition and its method of synthesis will be referred to hereinafter as "Inventive Embodiment I."

In an another embodiment of this invention, a polyol and a methyl diisocyanate were reacted to form a prepolymer. This prepolymer was reacted with a chain extender in the presence of an unsaturated carboxylic acid. The chain extended can be any internally saturated alpha-omega-dicarboxylic acid, such as, for example oleic or linoleic acids. Preferably, the chain extender is BDO. Thus, in this embodiment, an unsaturated functionality is substituted for the carboxyl group of Inventive Embodiment I. Preferably the unsaturated functionality is $$\overset{O}{\overset{\|}{HO-C}}-CH=CH-\overset{O}{\overset{\|}{C}}-OH.$$

The resulting unsaturated polymer was formed as illustrated below (V). This polymer was then reacted with a hydrophilic amine-terminated poly(ethylene oxide) (II) in the presence of a dehydrating agent as indicated below:

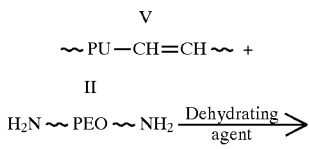

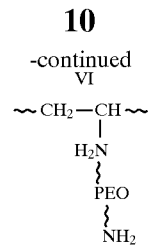

The product (VI) of the reaction indicated above is an unsaturated polymer-spacer complex characterized by an amine linkage between the spacer and the polymer. A bio-active agent then is grafted to the polymer-spacer complex in the presence of a dehydrating agent, such as, EDC as indicated below:

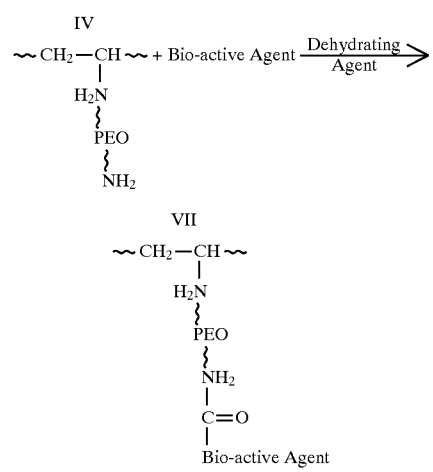

The product (VII) of the reaction indicated above is characterized by an amide linkage between the spacer and the bio-active molecule. Thus, in this embodiment, the reaction product (VII) is characterized by different linkages between its respective units, i.e., an amine linkage between the polyurethane backbone and the spacer and an amide linkage between the spacer and the bio-active agent. This composition and its method of synthesis will be referred to hereinafter as Inventive Embodiment II.

In Inventive Embodiments I and II, dehydrating agents are used to facilitate the reaction in which the spacer is covalently bound to the polyurethane backbone. Preferably, the chemical bond formed therebetween is either an amide or an amine chemical linkage. Similarly, dehydrating agents are used to facilitate the reaction in which the bio-active agent is covalently bound to the polyesterurethane backbone via the hydrophilic amine-terminated spacer. In this reaction, the linkage between the spacer and the bio-active agent is always an amide. Preferably, EDC catalyzes both of these reactions in the aqueous media of the present invention. In non-aqueous organic solvents many carbodiimides can be used, such as, for example, dicyclohexyl carbodiimide.

As Table 1 indicates, the present invention, e.g., Inventive Embodiments I and II, significantly improves upon previously described bio-active coating compositions and methods of making same, such as the Park Method described herein.

TABLE 1

|  | Park Method | Inventive Embodiment I | Inventive Embodiment II |
|---|---|---|---|
| Polymer Yield (gm/gm starting material) | 0.40 ± 0.5 | 1.05 ± 0.12 | 0.86 |
| Level of Polymer Cross-Linking | Moderate (1–60) | Negligible-Low (0–15) | Negligible-Low (0–25) |
| Factor Xa Heparin Activity μg/cm | 0.03–0.13 | 0.3–0.09 | 0.05 |

As illustrated in Table 1, the methods of the present invention provide for approximately a 100% increase in polymer yield while significantly decreasing the amount of polymer cross-linking, i.e. unwanted side-reactions and cross-sections, and without sacrificing heparin bio-activity.

The bio-active agent of the present invention is bound to the polymer backbone via a spacer group. The spacer group may include oxygenated polyolefins (e.g., polyvinyl alcohol), aliphatic polyesters, polyamino acids, polyamines, hydrophilic polysiloxanes, hydrophilic polysilazanes, hydrophilic acrylates, hydrophilic methacrylates, and linear or lightly branched polysaccharides. The spacer group is intended to be hydrophilic in order to take advantage of the natural repulsive forces of the hydrophobic substrate. The spacer group should have reactive functional groups on each end that are capable of reacting with and binding to the polymer backbone and bio-active agent respectively. Preferably, the spacer group has a functional group on each end, such as, a carboxylic acid group or an amine group. An amino end-blocked poly(ethylene oxide) is a preferred example.

Moreover, hydrophilic poly(ethylene oxide) spacers are preferred because they have low interfacial free energy, lack binding sites, and exhibit highly dynamic motion. These characteristics are important because they increase the activity of a PEO-linked bio-active agent, e.g., heparin. See, K. D. Park et al., supra.

As previously mentioned, the length of the spacer group may be used to control the bio-active agent's activity. It is known in the art that the anti-thrombogenic activity of heparin is increased when it is positioned a certain distance from the substrate to which it is bound. For example, in a comparison of polymer-spacer-heparin coatings using a $C_6$ alkyl spacer, PEO 200, PEO 1000 and PEO 4000, the polymer-PEO 4000-Heparin surface maintained the highest bio-activity. See, K. D. Park et al., supra. Thus, methods are available in the art for controlling the activity of a polymer-bound bio-active agent. By utilizing such methods, one may determine the optimal length of the spacer. Accordingly, as used herein, "effective distance" means the distance between the bound bio-active agent and the polymer backbone which corresponds to a desired level of activity in the bio-active agent.

Thus, in the present invention, control over the bio-active agent's activity is achieved by varying the length, e.g., molecular weight, of the spacer group. The spacer group may have a molecular weight of about 100 to about 200,000 daltons. Preferably, the spacer group has a molecular weight of about 200 to about 50,000 daltons. More preferably, the spacer group has a molecular weight of about 1,000 to about 10,000 daltons. Most preferably, the amino end-blocked poly(ethylene oxide) has a molecular weight of 4,000 daltons.

In accordance with the present invention, a significant reduction of thrombus formation and/or infection associated with the use of medical articles is achieved by combining an anti-thrombogenic and/or anti-infective agent in a coating to be applied to the host-contacting surface(s) of the article. A variety of anti-infective agents as known in the art may be used, including, antibiotics, such as penicillin and antibacterial agents such as silver sulfadiazine. Similarly, a variety of anti-thrombogenic agents known in the art may be used, including, heparin, prostaglandins, urokinase, streptokinase, sulfated polysaccharide, and albumin. In some cases it may be desirable to provide either dual anti-infective or anti-thrombogenic action with two or more agents. Additionally, it may be desirable to combine an anti-infective and an anti-thrombogenic action by combining two or more of these different agents. The invention will be described in terms of the preferred heparin, a known anti-thrombogenic agent of known safety and high anti-coagulation activity, with the understanding that the invention contemplates any anti-thrombogenic and/or anti-infective agent which may be grafted to the polymer backbone by the method of the present invention.

An article of the invention may be any medical article compatible with a polymer bound bio-active agent coating which, absent the coating, may lead to thrombus formation and/or infection when in contact with a body tissue or fluid. Exemplary of, but not limited to, such articles are vascular access (arterial and venous) catheters, introducers, vascular grafts, endoprosthesis, stents, urinary catheters and associated articles, such as drainage bags and connectors, and all abdominal cavity drainage tubing, bags and connectors. Preferred articles are polymeric, most preferably expandable polytetrafluoroethylene (ePTFE) small caliber vascular grafts. For purposes of this invention, "vascular grafts" is meant to include endoprostheses.

In yet another embodiment of the invention, an article is contacted with an aqueous solution containing one of the compositions of the present invention. All conventional methods of applying a coating to an article are contemplated by the invention. For example, the article may be dipped or steeped in such a solution, thus coating an appropriate surface of the article. Alternatively, a coating of one of the compositions of the invention may be sprayed onto a surface of the article. Preferably, the surface to be coated with a composition of the present invention is subjected to plasma treatment prior to application of one or more coats of the present invention. Most preferably, the luminal surface of a small caliber ePTFE vascular graft is prepared by treatment with a hydrogen-rich plasma followed by applying one or more coats of a composition of the invention.

In a further embodiment, the present invention includes a biocompatible polymer backbone having carboxyl functionality or unsaturated functionality, an amine-terminated spacer and a bio-active agent. In this embodiment, a dehydrating agent, such as 1-(-3-dimethylaminopropyl)-3-ethylcarbodiimide, may be used to facilitate binding of the polymer backbone to one end of the amine terminated spacer and of the bio-active agent to the other, non-reacted end of the spacer.

The invention being thus described, it will be obvious that the same may be varied in many ways. Such variations are not to be regarded as a departure from the spirit and scope of the invention and all such modifications are intended to be included within the scope of the following claims.

What is claimed is:

1. A polymer-bound bio-active composition represented by the structure:

wherein P is a biocompatible polymer selected from the group consisting of biocompatible polymers having carboxyl functionality, unsaturated functionality, and mixtures thereof; $R^1$ is O=C—NH or NH; $R^2$ is a hydrophilic amine-terminated spacer selected from the group consisting of oxygenated polyolefins, aliphatic polyesters, polyamino acids, polyamines, hydrophilic polysiloxanes, hydrophilic polysilazanes, hydrophilic acrylates, hydrophilic methacrylates, linear and lightly branched polysaccharides; and $R^3$ is a bio-active agent selected from the group consisting of anti-thrombogenic agents, antibiotic agents, antibacterial agents, antiviral agents, their pharmaceutical salts, and mixtures thereof.

2. The bio-active coating of claim 1, wherein said polymer backbone is a polyesterurethaneurea.

3. The bio-active coating of claim 1, wherein said hydrophilic amine-terminated spacer is an amino end-blocked poly(ethylene oxide).

4. The bio-active coating of claim 3, wherein said amino end-blocked poly(ethylene oxide) has a molecular weight of about 100 daltons to about 200,000 daltons.

5. The bio-active coating of claim 3, wherein said amino end-blocked poly(ethylene oxide) has a molecular weight of about 200 to about 50,000 daltons.

6. The bio-active coating of claim 3, wherein said amino end-blocked poly(ethylene oxide) has a molecular weight of about 1,000 to about 10,000 daltons.

7. The bio-active coating of claim 1, wherein said molecular weight of said hydrophilic amine-terminated spacer positions said bio-active agent at an effective distance from said polymer backbone.

8. The bio-active coating of claim 1, wherein said bio-active agent is heparin.

* * * * *

UNITED STATES PATENT AND TRADEMARK OFFICE
CERTIFICATE OF CORRECTION

PATENT NO. : 5,855,618
DATED : January 5, 1999
INVENTOR(S) : Patnaik et al.

It is certified that error appears in the above-identified patent and that said Letters Patent is hereby corrected as shown below:

Column 1, Line 64, now reads "jonically", should read --ionically--;

Column 4, Line 18, now reads "allophanatelbiuret", should read --allophanate/biuret--.

Signed and Sealed this

Ninth Day of November, 1999

Attest:

Q. TODD DICKINSON

Attesting Officer

Acting Commissioner of Patents and Trademarks